US00PP34519P2

(12) United States Plant Patent
Van Swieten

(10) Patent No.: US PP34,519 P2
(45) Date of Patent: Aug. 23, 2022

(54) ***PHALAENOPSIS* ORCHID PLANT NAMED 'PHA393573'**

(50) Latin Name: ***Phalaenopsis* hybrid**
Varietal Denomination: 'PHA393573'

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,244

(22) Filed: Mar. 30, 2022

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHA393573', particularly characterized by having reddish-purple and striped flowers with light purple edges and dark purplish-red lips, flowers that are concave in lateral view, panicle inflorescence, and is propagated by meristem tissue culture, is disclosed.

3 Drawing Sheets

Genus and species: *Phalaenopsis* hybrid.
Variety denomination: 'PHA393573'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA393573'.

The new *Phalaenopsis* plant is a product of a planned breeding program conducted by the inventor in Bleiswijk, the Netherlands. The objective of this breeding program was to create a new *Phalaenopsis* plant with numerous attractive, reddish-purple, and striped flowers with light purple edges and dark purplish-red lips, suitable for potted plant production.

The new *Phalaenopsis* plant 'PHA393573' is a result of cross-pollination made by the inventor in March 2014 in Bleiswijk, the Netherlands, of the proprietary female, or seed parent, *Phalaenopsis* hybrid 'PHALUFREL' (U.S. Plant Pat. No. 29,259) with the proprietary male, or pollen parent, *Phalaenopsis* hybrid '47474-02' (unpatented).

The new *Phalaenopsis* was selected by the inventor as a single plant within the progeny of the stated cross-pollination in a controlled greenhouse in Bleiswijk, the Netherlands, in December 2016. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1109), by Applicant who obtained the subject matter disclosed directly from the inventor. 'PHA393573' has not been made publicly available or sold anywhere in the world prior to the effective filing date of this application with the exception of sales or disclosures made one year or less before the effective filing date of this claimed invention by Applicant who obtained 'PHA393573' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA393573' as a new and distinct variety of *Phalaenopsis* plant:

1) Reddish-purple and striped flowers with light purple edges and dark purplish-red lips;
2) Flower shape in lateral view is concave; and
3) Appearance of inflorescence is panicle.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2022. Colors in the photographs may differ from the color values cited in the detailed botanical description, which accurately describe the actual colors of the new variety.

DESCRIPTION OF THE NEW VARIETY

Figure 1:
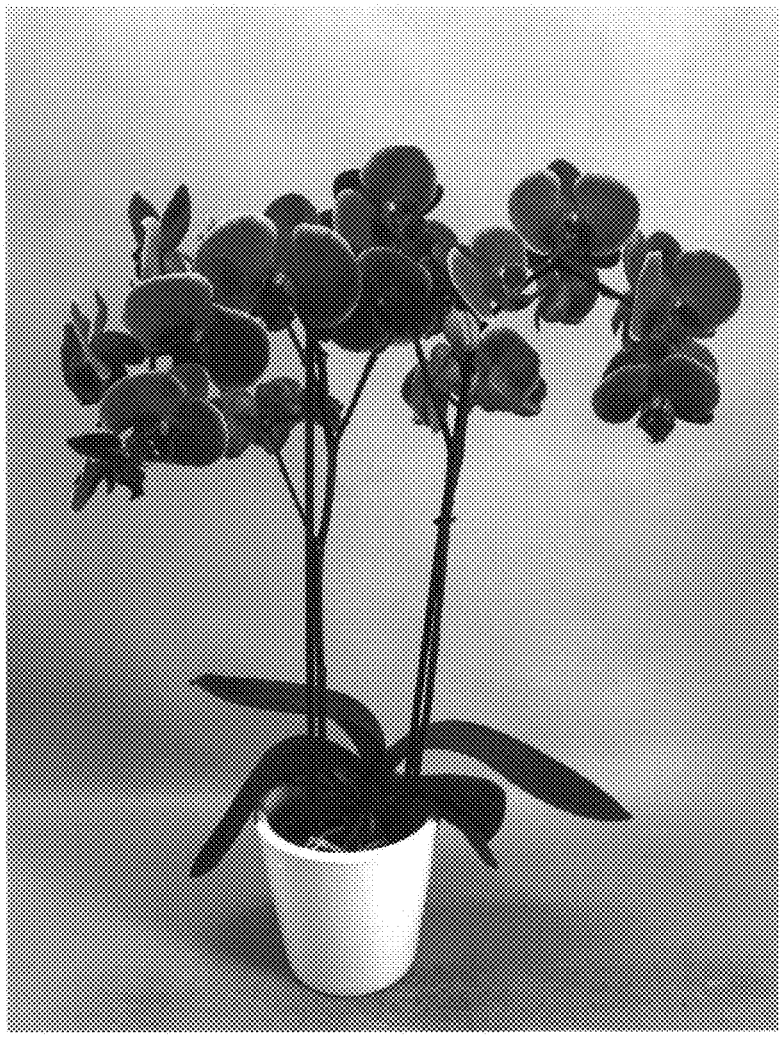
FIG. 1 shows the overall plant habit, including blooms, buds, and foliage of 'PHA393573'.
Figure 2:
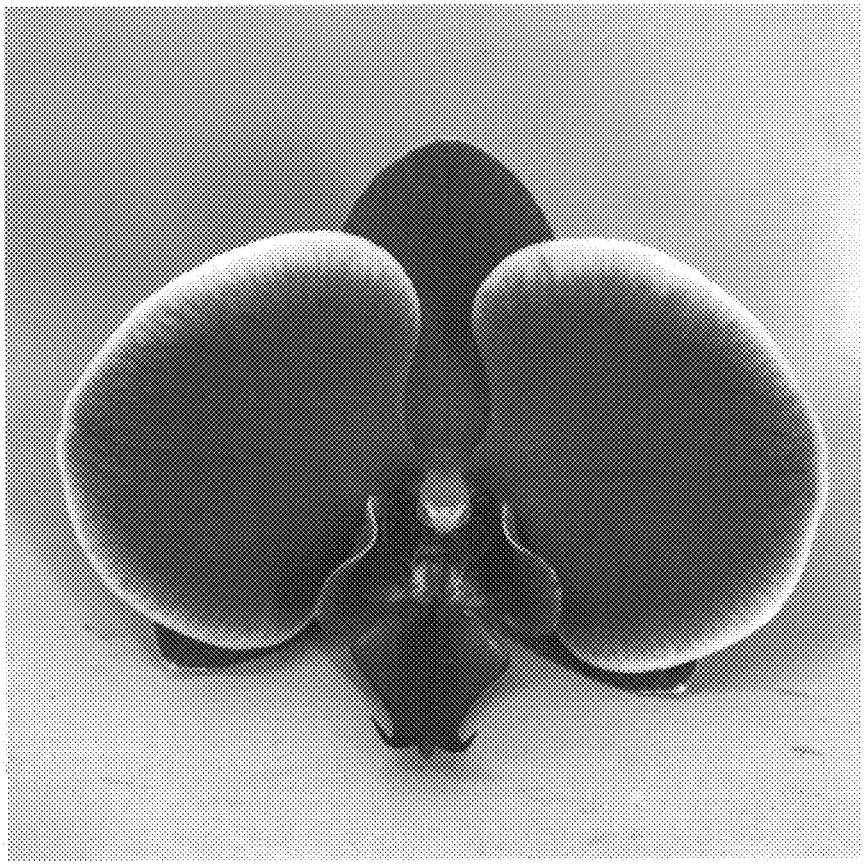
FIG. 2 shows a close-up of a flower of 'PHA393573'.
Figure 3:
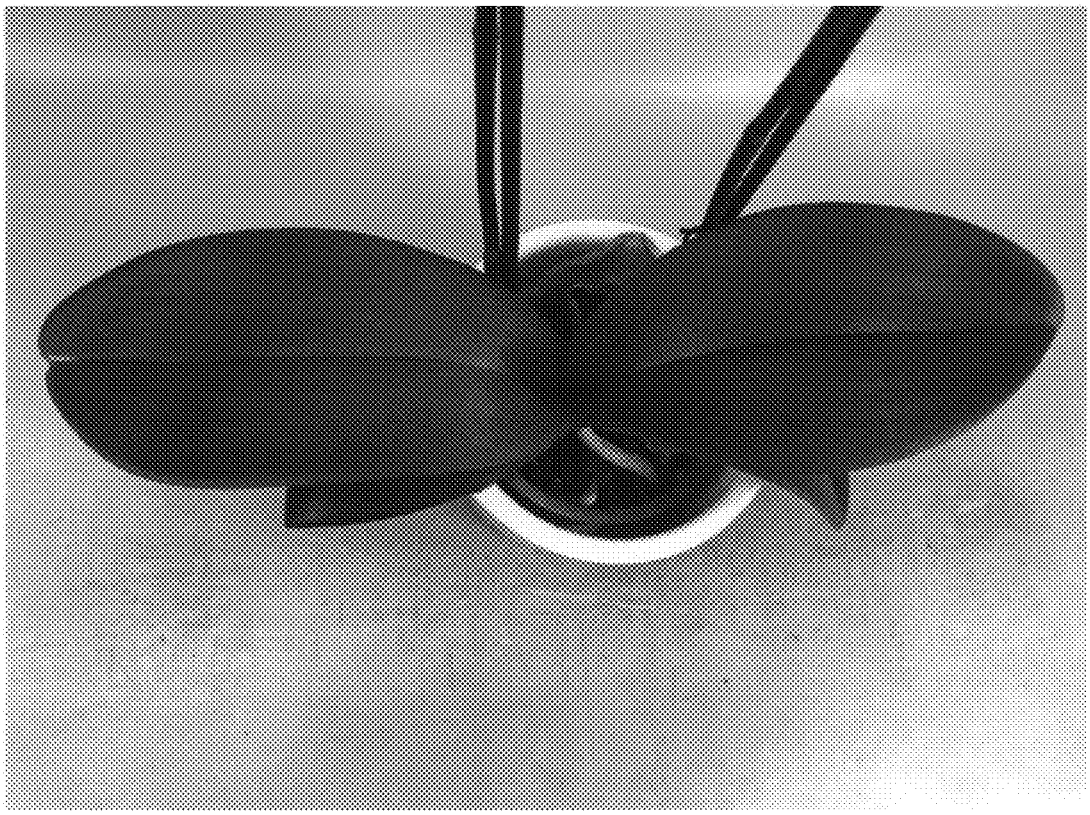
FIG. 3 shows an overhead view of the leaves of 'PHA393573'.

The following detailed description sets forth the distinctive characteristics of 'PHA393573'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA393573'.

Parentage:

*Female parent*.—*Phalaenopsis* cultivar 'PHALUFREL' (U.S. Plant Pat. No. 29,259).

*Male parent*.—*Phalaenopsis* cultivar '47474-02' (unpatented).

Propagation:

*Type*.—Meristem tissue culture.

Roots:

*Root description*.—Greyed-green (a color in between RHS 190B and RHS 190C) colored roots with branching lateral roots having yellowish-green (RHS N144A) with a touch of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 56.0 cm to 61.0 cm.

*Width* (*measured from leaf tips*).—About 32.0 cm to 36.0 cm.

*Vigor*.—Strong.

Leaves:

*Mature leaves*.—Quantity per plant: 6 to 7 leaves are produced before flowering. Length (fully expanded): 19.0 cm to 21.0 cm. Width: 8.5 cm to 9.5 cm. Position of the broadest part of the leaf: At the middle. Shape: Oblong. Base shape: Moderately elongated. Apex: Obtuse asymmetric. Leaf blade angle with the petiole (measured from the horizontal position): Between 10 degrees and 30 degrees. Leaf margin: Entire. Color: Upper surface: RHS 147A. Lower surface: RHS 146A with a purple margin (RHS N77A) toward the tip. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146B.

Peduncle:

*Quantity per plant*.—1 to 2.

*Number of flowers per peduncle*.—12 to 16.

*Length*.—51.0 cm to 61.0 cm.

*Diameter*.—5.0 mm to 6.0 mm.

*Strength*.—Strong.

*Aspect*.—Upright to slightly pendent.

*Texture*.—Smooth.

*Color*.—Brown (RHS 200A) with a touch of yellow-green (RHS 147C).

*Internode length*.—3.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 280.0 mm to 330.0 mm.

*Flowering time*.—First flowers can be expected 10 to 11 months after planting in a 12-cm pot.

*Flower*.—Height: 73.0 mm to 78.0 mm. Diameter: 85.0 mm to 90.0 mm. Depth of lip: 23.0 mm to 25.0 mm.

*Flower shape*.—Concave.

*Flower longevity*.—On the plant: 10 to 12 weeks.

*Fragrance*.—Absent.

*Flower bud*.—Average size: Large. Length: 21.0 mm to 23.0 mm. Width: 20.0 mm to 22.0 mm. Shape: Egg shaped. Color: Yellow-green (RHS 144C) at the base with a dark purple-red shade (a color in between RHS N79B and RHS N77B) and dark purple stripes (RHS N79B).

*Petals*.—Arrangement: Open/free. Shape: Semi-circular. Apex: Emarginated asymmetric. Margin: Entire. Length (from base to tip): 38.0 mm to 40.0 mm. Width: 52.0 mm to 54.0 mm. Position of the broadest part of the petal: Toward the base. Color (when fully opened): Upper surface: Basic color: Reddish-purple (a color in between RHS N78A and RHS NN78A). Over color: Light purple edge (RHS 76A); dark red-purple stripes (a color in between RHS N79C and RHS N78A). Lower surface: Basic color: Reddish-purple (RHS N78B). Over color: Touch of light yellow-green (RHS 145C) at the base; purplish-pink (RHS N78C) at the middle; very light purple edge (RHS 76B); dark red-purple stripes (a color in between RHS N79C and RHS N78A). Number of spots and stripes on the petals (upper surface): Many stripes. Color of spots and stripes on the petals (upper surface): A color in between RHS N79C and RHS N78A. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 43.0 mm to 45.0 mm. Width: 32.0 mm to 34.0 mm. Position of the broadest part of the dorsal sepals: At the middle. Color (when fully opened): Upper surface: Basic color: Reddish-purple (RHS N78A). Over color: Dark purplish-red shade (a color in between RHS N79C and RHS N78A) and very small light reddish-purple dots (RHS N78D) and dark red-purple stripes (a color in between RHS N79C and RHS N79D). Lower surface: Basic color: Reddish-purple (RHS N78B). Over color: Yellowish-green (RHS 195B) at the middle from the base and reddish-purple stripes (a color in between RHS N78A and RHS N78B). Number of spots, dots, and stripes on the dorsal sepals (upper surface): Medium stripes and many of very small dots. Color of spots, dots, and stripes on the dorsal sepals (upper surface): Stripes (a color in between RHS N79C and RHS N79D) and dots (RHS N78D). Density of netting of the dorsal sepals (upper surface): Low. Color of the netting (upper surface): A color in between RHS N79C and RHS N79D.

*Lateral sepals*.—Shape: Ovate. Apex: Obtuse asymmetric. Margin: Entire. Length (from base to tip): 42.0 mm to 44.0 mm. Width: 29.0 mm to 31.0 mm. Position of the broadest part of the lateral sepals: Toward the base. Color (when fully opened): Upper surface: Basic color: Reddish-purple (a color in between RHS N78A and RHS N79C). Over color: Touch of light yellow-green (RHS 144C) at the base; dark purplish shade (RHS N79C) on one side; stripes (a color in between RHS N79C and RHS 187B); very small dots (RHS N78D). Lower surface: Basic color: Purplish-pink (RHS N78C). Over color: Light yellow-green (a color in between RHS 145C and RHS 145D); purplish-pink shade (RHS N78C) and reddish-purple stripes (a color in between RHS N78A and RHS N78B). Number of spots, dots, and stripes on the lateral sepals (upper surface): Medium stripes and medium of very small dots. Color of spots, dots, and stripes on the lateral sepals (upper surface): Stripes (a color in between RHS N79C and RHS 187B) and dots (RHS N78D). Density of netting of the lateral sepals (upper surface): Medium. Color of the netting (upper surface): RHS 187B.

*Labellum* (*lip*).—Whiskers: Present. Length of whiskers: 5.0 mm to 7.0 mm. Color of whiskers: Dark purplish-red (RHS N79C) at the base; dark red (RHS 187B) with very small white tips (RHS 155B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 20.0 mm to 22.0 mm. Width: 15.0 mm to 17.0 mm. Color: Upper surface: Touch of yellow (RHS 9A) at the base; dark red (RHS 187C) and reddish-purple (RHS N78A) toward margins. Lower surface: Touch of yellowish-white (RHS 196D) and yellow (RHS 9B) at the base; dark purplish-red (RHS N79C) toward margin on one side and reddish-purple (RHS N78B) toward margin on the other side. Number of spots and stripes on the lateral lobe: None. Color of spots and stripes on the lateral lobe: Not applicable. Density of netting of the lateral lobe: None. Color of the netting: None.

*Apical lobe*.—Shape: Trullate. Margin: Entire. Length: 19.0 mm to 21.0 mm. Width: 18.0 mm to 20.0 mm. Color: Upper surface: Touch of yellow (RHS 9A) at the base toward wings margin; dark purplish-red (RHS N79C); dark red shade (RHS 59A) at the middle and dark red middle vein (RHS 187A). Lower surface: Yellowish-white (RHS 196D) at the middle from the base toward the tip and touch of yellow (RHS 163C) at the base of wings; reddish-purple (RHS N78A) and dark purplish-red (RHS N79C) toward the margins. Number of spots and stripes on the apical lobe: None. Color of spots and stripes on the apical lobe: None. Density of netting of the apical lobe: None. Color of the netting: None. Bump and ridge: Medium.

*Callus*.—Average size: Medium. Height: 6.0 mm to 7.0 mm. Length: 6.0 mm to 7.0 mm. Width: 4.0 mm to 5.0 mm. Color: Light greenish-yellow (RHS 4C); light greenish-yellow tips (RHS 5C); dotted (RHS 183A on front and RHS 176A on sides).

Reproductive organs:

*Column*.—Length: 9.0 mm to 10.0 mm. Diameter: 5.0 mm to 6.0 mm. Color: Reddish-purple (RHS N78A) at the base; lighter reddish-purple (RHS N78B) toward the tip.

*Pollinia*.—Quantity: 2. Diameter: 0.9 mm to 1.1 mm. Color: Orange-yellow (RHS 23A).

*Ovary*.—Length: 9.0 mm to 12.0 mm. Diameter: 2.3 mm to 2.6 mm.

*Pedicel*.—Length: 36.0 mm to 38.0 mm. Diameter: 2.8 mm to 3.2 mm. Color: Brown (RHS N200A) at the base and yellow-green (RHS 145B) with a touch of light purple (RHS 75A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA393573' differs from the female parent plant 'PHALUFREL' (U.S. Plant Pat. No. 29,259) in that 'PHA393573' has emarginated petal apexes and flowers with a medium area of edge pattern, whereas 'PHALUFREL' has rounded petal apexes and flowers with a large area of edge pattern.

'PHA393573' differs from the male parent plant '47474-02' (unpatented) in that 'PHA393573' has panicle inflorescence and obtuse dorsal sepal apexes, whereas '47474-02' has raceme inflorescence and rounded dorsal sepal apexes.

'PHA393573' is most similar to the commercial *Phalaenopsis* plants named 'PHALHITWOQ' (U.S. Plant Pat. No. 32,283) and 'PHALGLAOR' (U.S. Plant Pat. No. 31,482). 'PHA393573' differs from the commercial variety 'PHALHITWOQ' in that 'PHA393573' has flowers that are concave in lateral view and trullate apical lobes, whereas 'PHALHITWOQ' has flowers that are flat in lateral view and triangular apical lobes. Additionally, 'PHA393573' has smaller flowers and shorter whiskers than 'PHALHITWOQ'.

'PHA393573' differs from the commercial variety 'PHALGLAOR' in that 'PHA393573' has flowers that are concave in lateral view, whereas 'PHALGLAOR' has flowers that are flat in lateral view. Additionally, 'PHA393573' has narrower apical lobes and shorter whiskers than 'PHALGLAOR'.

I claim:

1. A new and distinct variety of *Phalaenopsis* plant named 'PHA393573', substantially as described and illustrated herein.

* * * * *